(12) United States Patent
Lane (10) Patent No.: US 8,784,361 B2
(45) Date of Patent: Jul. 22, 2014

(54) COMBINED COAXIAL AND BIMANUAL IRRIGATION/ASPIRATION APPARATUS

(75) Inventor: Stephen Lane, Shoreview, MN (US)

(73) Assignee: Alcon Research, Ltd., Fort Worth, TX (US)

( * ) Notice: Subject to any disclaimer, the term of this patent is extended or adjusted under 35 U.S.C. 154(b) by 362 days.

(21) Appl. No.: 12/962,082

(22) Filed: Dec. 7, 2010

(65) Prior Publication Data

US 2012/0143125 A1   Jun. 7, 2012

(51) Int. Cl.
*A61M 3/00* (2006.01)
(52) U.S. Cl.
USPC .................. 604/43; 604/39; 604/294
(58) Field of Classification Search
CPC ............ A61M 1/0039; A61M 1/0058; A61M 1/0062; A61M 1/0064; A61M 1/0084; A61M 39/10; A61M 2210/0612; A61B 5/150519; A61B 17/3203; A61B 2017/320084; A61F 9/00736
USPC ........... 604/27, 35, 39, 40, 43, 289, 294, 521, 604/44, 45; 433/91, 92, 95, 96
See application file for complete search history.

(56) References Cited

U.S. PATENT DOCUMENTS

| 3,805,787 A | 4/1974 | Banko |
|---|---|---|
| 4,014,333 A | 3/1977 | McIntyre |
| 4,047,532 A | 9/1977 | Phillips et al. |
| 4,204,328 A | 5/1980 | Kutner |
| 4,386,927 A | 6/1983 | Eichenbaum |
| 4,445,509 A | 5/1984 | Auth |
| 4,487,600 A | 12/1984 | Brownlie et al. |
| 4,519,385 A * | 5/1985 | Atkinson et al. .............. 601/161 |
| 4,531,943 A | 7/1985 | Van Tassel et al. |
| 4,573,979 A | 3/1986 | Blake |
| 4,652,255 A | 3/1987 | Martinez |
| 4,710,180 A | 12/1987 | Johnson |

(Continued)

FOREIGN PATENT DOCUMENTS

| DE | 4313245 | 3/1997 |
|---|---|---|
| DE | 197 00 809 A1 | 7/1998 |

(Continued)

OTHER PUBLICATIONS

International Searching Authority, International Search Report, PCT/US2011/030751, Feb. 6, 2012, 3 pages.

(Continued)

*Primary Examiner* — Kami A Bosworth
(74) *Attorney, Agent, or Firm* — Kenneth D. Bassinger (57) ABSTRACT

In one exemplary aspect, the present disclosure is directed to an assembly having an irrigation hand piece that includes an irrigation needle extending from a distal end. The irrigation needle is also configured to release a first fluid. The assembly further has an aspiration hand piece that includes an aspiration needle extending from a distal end. The aspiration needle has an axis and is configured to aspirate a second fluid into the assembly. The assembly has a first configuration in which the irrigation hand piece and aspiration hand piece are coupled together in a manner that causes the released first fluid from the assembly to flow coaxially about the axis of the aspiration needle and a second configuration in which the irrigation hand piece and aspiration hand piece are uncoupled which causes the released first fluid to flow substantially non-coaxial with respect to the axis of the aspiration needle.

13 Claims, 3 Drawing Sheets

(56) References Cited

U.S. PATENT DOCUMENTS

| | | |
|---|---|---|
| 4,717,387 A | 1/1988 | Inoue et al. |
| 4,813,926 A | 3/1989 | Kerwin |
| 4,878,900 A | 11/1989 | Sundt |
| 4,897,079 A | 1/1990 | Zaleski et al. |
| 4,904,238 A | 2/1990 | Williams |
| 4,921,482 A | 5/1990 | Hammerslag et al. |
| 4,983,160 A | 1/1991 | Steppe et al. |
| 4,998,916 A | 3/1991 | Hammerslag et al. |
| 4,998,923 A | 3/1991 | Samson et al. |
| 5,037,391 A | 8/1991 | Hammerslag et al. |
| 5,084,009 A | 1/1992 | Mackool |
| 5,084,012 A | 1/1992 | Kelman |
| 5,106,381 A | 4/1992 | Chikama |
| 5,108,368 A | 4/1992 | Hammerslag et al. |
| 5,133,159 A | 7/1992 | Nelson |
| 5,151,084 A | 9/1992 | Khek |
| 5,176,126 A | 1/1993 | Chikama |
| 5,203,772 A | 4/1993 | Hammerslag et al. |
| 5,217,465 A | 6/1993 | Steppe |
| 5,242,449 A | 9/1993 | Zaleski |
| 5,286,256 A | 2/1994 | Mackool |
| 5,290,892 A | 3/1994 | Namdaran et al. |
| 5,292,310 A | 3/1994 | Yoon |
| 5,308,324 A | 5/1994 | Hammerslag et al. |
| 5,328,456 A | 7/1994 | Horiguchi |
| 5,354,265 A | 10/1994 | MacKool |
| 5,358,507 A | 10/1994 | Daily |
| 5,364,405 A | 11/1994 | Zaleski |
| 5,372,587 A | 12/1994 | Hammerslag et al. |
| 5,378,234 A | 1/1995 | Hammerslag et al. |
| 5,381,782 A | 1/1995 | Delarama et al. |
| 5,403,901 A | 4/1995 | Namdaran et al. |
| 5,421,955 A | 6/1995 | Lau et al. |
| 5,433,746 A | 7/1995 | Namdaran et al. |
| 5,441,496 A | 8/1995 | Easley et al. |
| 5,451,229 A | 9/1995 | Geuder et al. |
| 5,514,086 A | 5/1996 | Parisi et al. |
| 5,522,826 A | 6/1996 | Daily |
| 5,603,710 A | 2/1997 | Easley et al. |
| 5,645,530 A | 7/1997 | Boukhny et al. |
| 5,718,677 A | 2/1998 | Capetan et al. |
| 5,830,192 A | 11/1998 | Van Voorhis |
| 5,836,926 A | 11/1998 | Peterson et al. |
| 5,873,851 A | 2/1999 | Nilsson |
| 5,921,998 A | 7/1999 | Tano et al. |
| 5,957,928 A | 9/1999 | Kirwan, Jr. |
| 5,989,209 A | 11/1999 | Barrett |
| 6,007,513 A | 12/1999 | Anis et al. |
| 6,007,555 A | 12/1999 | Devine |
| 6,013,049 A | 1/2000 | Rockley et al. |
| 6,068,641 A | 5/2000 | Varsseveld |
| 6,117,151 A | 9/2000 | Urich et al. |
| 6,132,426 A | 10/2000 | Kroll |
| 6,299,591 B1 | 10/2001 | Banko et al. |
| 6,340,355 B1 | 1/2002 | Barrett |
| 6,398,759 B1 | 6/2002 | Sussman et al. |
| 6,428,501 B1 | 8/2002 | Reynard |
| 6,491,670 B1 | 12/2002 | Toth et al. |
| 6,520,929 B2 | 2/2003 | Zaleski |
| 6,544,254 B1 | 4/2003 | Bath |
| 6,579,270 B2 | 6/2003 | Sussman et al. |
| 6,592,541 B1 | 7/2003 | Kurwa |
| 6,623,477 B1 | 9/2003 | Elbrecht et al. |
| 6,852,093 B1 | 2/2005 | Boukhny |
| 6,902,558 B2 | 6/2005 | Laks |
| 7,014,629 B2 | 3/2006 | MacKool |
| 7,066,923 B2 | 6/2006 | Tjia |
| 7,094,229 B2 | 8/2006 | Boukhny et al. |
| 7,329,261 B2 | 2/2008 | Perkins |
| 2003/0004455 A1 | 1/2003 | Kadziauskas et al. |
| 2003/0069594 A1 | 4/2003 | Rockley et al. |
| 2003/0199883 A1 | 10/2003 | Laks |
| 2003/0208218 A1 | 11/2003 | Kadziauskas et al. |
| 2004/0068270 A1 | 4/2004 | Allred |
| 2004/0089080 A1 | 5/2004 | Kadziauskas |
| 2004/0092921 A1 | 5/2004 | Kadziauskas et al. |
| 2004/0153093 A1 | 8/2004 | Donovan |
| 2005/0171469 A1* | 8/2005 | Cunningham ............... 604/43 |
| 2005/0234473 A1 | 10/2005 | Zacharias |
| 2005/0256462 A1 | 11/2005 | Underwood |
| 2005/0277898 A1 | 12/2005 | Dimalanta et al. |
| 2005/0288650 A1 | 12/2005 | Boukhny et al. |
| 2006/0036215 A1 | 2/2006 | Boukhny |
| 2006/0047241 A1 | 3/2006 | Boukhny |
| 2006/0212038 A1 | 9/2006 | Boukhny |
| 2007/0244425 A1* | 10/2007 | Pond ............................ 604/27 |
| 2008/0167604 A1 | 7/2008 | Hong |
| 2010/0121260 A1 | 5/2010 | Ghannoum et al. |

FOREIGN PATENT DOCUMENTS

| | | |
|---|---|---|
| EP | 0778 039 A1 | 6/1997 |
| EP | 1371347 | 12/2003 |
| EP | 1607076 A1 | 12/2005 |
| EP | 1607077 | 12/2005 |
| EP | 1852095 | 11/2007 |
| FR | 2713492 A1 | 6/1995 |
| JP | 10071166 | 3/1998 |
| WO | WO 98/07398 | 2/1998 |
| WO | 99/11313 A1 | 3/1999 |
| WO | WO 02/28449 A2 | 4/2002 |
| WO | WO 02/28449 A3 | 9/2002 |
| WO | 20071006466 A1 | 1/2007 |
| WO | 20101056448 A1 | 5/2010 |
| WO | WO 2012/078319 A1 | 6/2012 |

OTHER PUBLICATIONS

International Searching Authority, Written Opinion of the International Searching Authority, PCT/US2011/030751, Feb. 6, 2012, 4 pages.

Dr. Ulrich Naumann, Notice of Opposition and EPO Communication, Sep. 23, 2010, 44 pages.

The ALCON Silicone I/A Tip, Alcon Inc., 2007, CAT281, 2 pages.

International Searching Authority, International Search Report, PCT/US2009/060315, Jan. 12, 2010, 4 pages.

International Searching Authority, Written Opinion of the International Searching Authority, PCT/US2009/060315, Jan. 12, 2010, 6 pages.

Prosecution History of European Patent No. 1852095, filed Apr. 25, 2007.

Dr. Ulrich Naumann, English translation of Opposition letter, Sep. 27, 2012, 7 pages.

English translation of Sep. 26, 2011 submission and English translation of Opponent letter dated Aug. 31, 2011, 6 pages.

* cited by examiner

COMBINED COAXIAL AND BIMANUAL IRRIGATION/ASPIRATION APPARATUS

BACKGROUND OF THE INVENTION

The present disclosure relates generally to a combined coaxial and bimanual irrigation/aspiration (I/A) surgical instrument used in surgical procedures such as, for example, a phacoemulsification procedure.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens.

In the United States, the majority of cataractous lenses are removed by a surgical technique called phacoemulsification. In the past, two different types of surgical instruments have been used during a phacoemulsification procedure, namely a coaxial instrument or a bimanual instrument. A typical coaxial instrument suitable for phacoemulsification procedures includes of an ultrasonically driven phacoemulsification hand piece, an attached hollow cutting needle surrounded by an irrigating sleeve, and an electronic control console. The hand piece assembly is attached to the control console by an electric cable and flexible tubing. Through the electric cable, the console varies the power level transmitted by the hand piece to the attached cutting needle. The flexible tubing supplies irrigation fluid to the surgical site and draws aspiration fluid from the eye through the hand piece assembly.

During the phacoemulsification procedure using the coaxial instrument, the tip of the cutting needle and the end of the irrigation sleeve are inserted into the anterior capsule of the eye through an incision in the outer tissue of the eye. The surgeon brings the tip of the cutting needle into contact with the lens of the eye, so that the vibrating needle tip fragments the lens. The resulting fragments are aspirated out of the eye through the interior bore of the cutting needle, along with irrigation solution provided to the eye during the procedure, and into a waste reservoir. However, because the irrigating sleeve surrounds the needle, the incision size necessary for insertion of the coaxial instrument into the eye has to be large enough to accommodate for the diameter of the coaxial instrument (e.g. the diameter of the end of the irrigation sleeve surrounding the tip of the cutting). Thus, while the coaxial instrument advantageously allows for a single piece instrument to perform irrigation and aspiration, its larger diameter size requires a large accommodating incision introducing more trauma at the surgical site.

The alternative surgical instrument used during a phacoemulsification procedure is commonly referred to as a bimanual instrument. The bimanual instrument, as the name implies, is actually two physically separate instruments. In that regard, one of the instruments is for irrigation and the other instrument is for aspiration. The aspiration instrument typically includes an ultrasonically driven phacoemulsification hand piece and an attached hollow cutting needle. The irrigation instrument includes a hand piece and an attached irrigation needle having irrigation ports. The aspiration and irrigation instruments are attached to a control console by electric cabling and flexible tubing. Through the electric cable, the console varies the power level transmitted by the hand piece to the attached cutting needle. The flexible tubing supplies irrigation fluid to the surgical site through the irrigation needle and draws aspiration fluid from the eye through the cutting needle.

During the phacoemulsification procedure using the bimanual instrument, the tips of the cutting and irrigation needles are inserted into the anterior capsule of the eye. Because the bimanual instrument is actually two separate instruments, the surgeon can make two separate incisions into the eye. Accordingly, the surgeon can insert the tips of the cutting needle and the irrigation needle into the separate incision sites. This allows for smaller incision sizes in the eye when compared to the phacoemulsification procedure using the coaxial instrument discussed above. Moreover, because the aspiration instrument does not have an irrigation sleeve surrounding the cutting needle, the diameter of the diameter of the distal end of the aspiration instrument is smaller than the distal end of the coaxial instrument. Again, this allows for a smaller incision sizes for the tip of the cutting needle for insertion into the eye when compared to the phacoemulsification procedure using the coaxial instrument discussed above. However, because a surgeon requires both aspiration and irrigation during a phacoemulsification procedure, typically both of the surgeon's hands are occupied with a respective instrument. Thus, during a phacoemulsification procedure using the bimanual instrument, the surgeon typically does not have an unoccupied or free hand available to further assist the surgeon.

The systems, devices, and methods disclosed herein overcome at least one of the shortcomings in the prior art.

SUMMARY OF THE INVENTION

In one exemplary aspect, the present disclosure is directed to an assembly. The assembly has an irrigation hand piece that includes an irrigation needle extending from a distal end of the irrigation hand piece. The irrigation needle is also configured to release a first fluid from the assembly. The Assembly further has an aspiration hand piece that includes an aspiration needle extending from a distal end of the aspiration hand piece. The aspiration needle has an axis and is configured to aspirate a second fluid into the assembly. The assembly has a first configuration in which the irrigation hand piece and aspiration hand piece are coupled together in a manner that causes the released first fluid from the assembly to flow coaxially about the axis of the aspiration needle. The assembly has a second configuration in which the irrigation hand piece and aspiration hand piece are uncoupled which causes the released first fluid to flow substantially non-coaxial with respect to the axis of the aspiration needle.

In one exemplary aspect, the present disclosure is directed to an assembly. The assembly has an irrigation hand piece that includes an irrigation needle extending from a distal end of the irrigation hand piece.

The irrigation needle configured to release a first fluid from the assembly.

The assembly further includes an aspiration hand piece including an aspiration needle extending from a distal end of the aspiration hand piece. The aspiration needle having an axis and being configured to aspirate a second fluid into the assembly. The sleeve member selectively attachable to the irrigation and aspiration hand pieces and shaped so that when in a first configuration the sleeve member couples the irrigation hand piece and the aspiration hand piece together in a manner that causes the released first fluid from the assembly to flow coaxially about the axis of the aspiration needle and a second configuration detached from the irrigation hand piece and the aspiration hand piece that causes the released first fluid to flow substantially non-coaxial with respect to the axis of the aspiration needle.

In one exemplary aspect, a method for using an assembly. The method includes providing an irrigation hand piece including an irrigation needle extending from a distal end of the irrigation hand piece. The irrigation needle configured to release a first fluid from the assembly. The method includes providing an aspiration hand piece including an aspiration needle extending from a distal end of the aspiration hand piece. The aspiration needle having an axis and being configured to aspirate a second fluid into the assembly. The method includes assembling a coaxial irrigation and aspiration device by coupling the irrigation hand piece and the aspiration hand piece together in a manner that causes the released first fluid from the assembly to flow coaxially about the axis of the aspiration needle.

These and other aspects, forms, objects, features, and benefits of the present disclosure will become apparent from the following detailed drawings and description.

BRIEF DESCRIPTION OF THE DRAWINGS

The accompanying drawings, which are incorporated in and constitute a part of the specification, illustrate embodiments of the present disclosure. Together with a general description of the present disclosure given above, and the detailed description given below, the drawings serve to exemplify the embodiments of the present disclosure.

DETAILED DESCRIPTION OF THE INVENTION

The present disclosure relates generally to the field of ophthalmic surgery, and more particularly to a combined coaxial and bimanual irrigation/aspiration (I/A) surgical instrument used in, for example, a phacoemulsification procedure. For the purposes of promoting an understanding of the principles of the present disclosure, reference will now be made to embodiments or examples illustrated in the drawings, and specific language will be used to describe these examples. It will nevertheless be understood that no limitation of the scope of the present disclosure is thereby intended. Any alteration and further modifications in the described embodiments, and any further applications of the principles of the present disclosure as described herein are contemplated as would normally occur to one skilled in the art to which the disclosure relates.

Figures 1, 2:
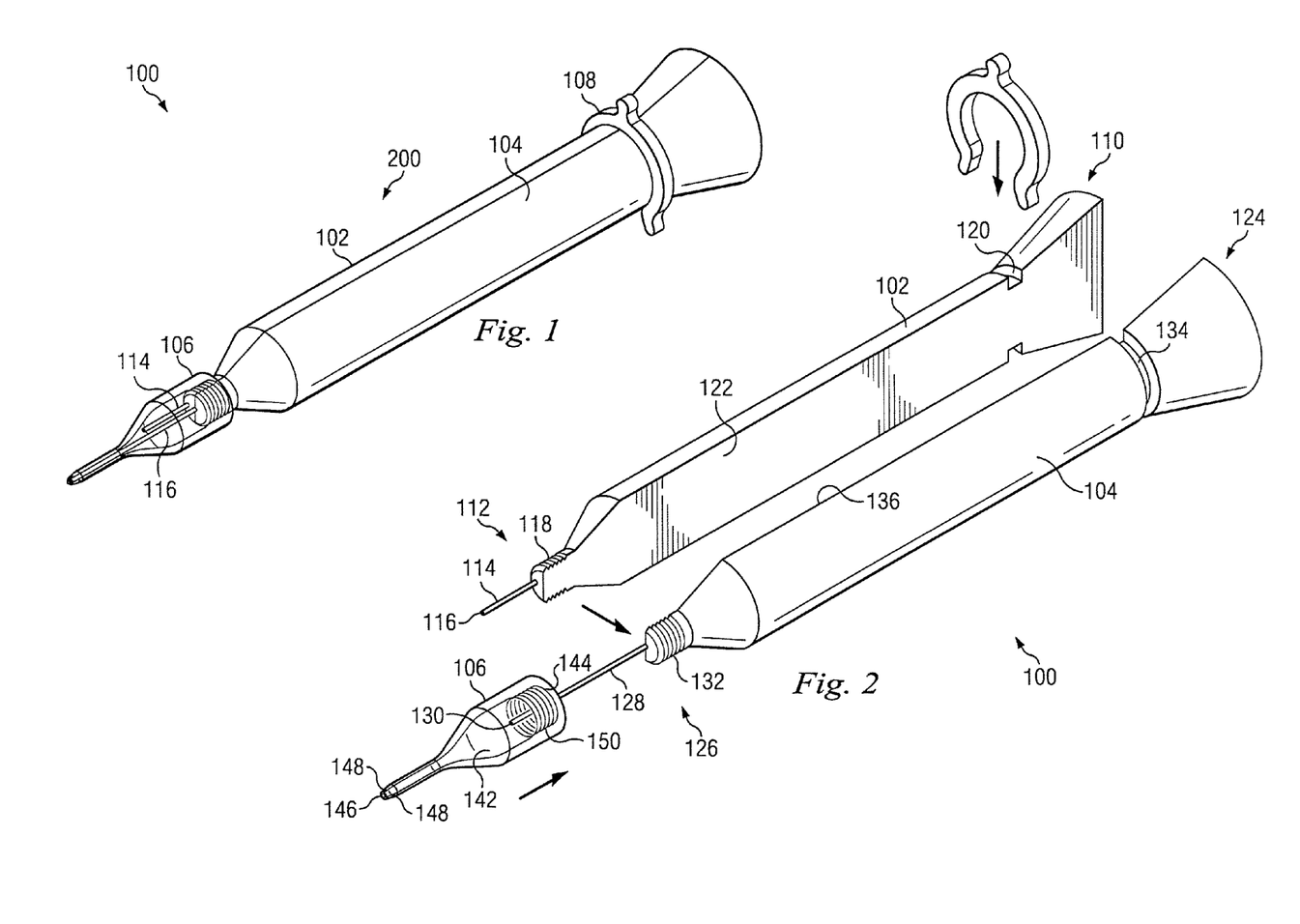
FIG. 1 is an illustration of a perspective view of an assembly providing a combined coaxial and bimanual I/A surgical instrument according to one aspect of the present disclosure.
FIG. 2 is an illustration of am exploded perspective view of the assembly of FIG. 1.
Figure 3:
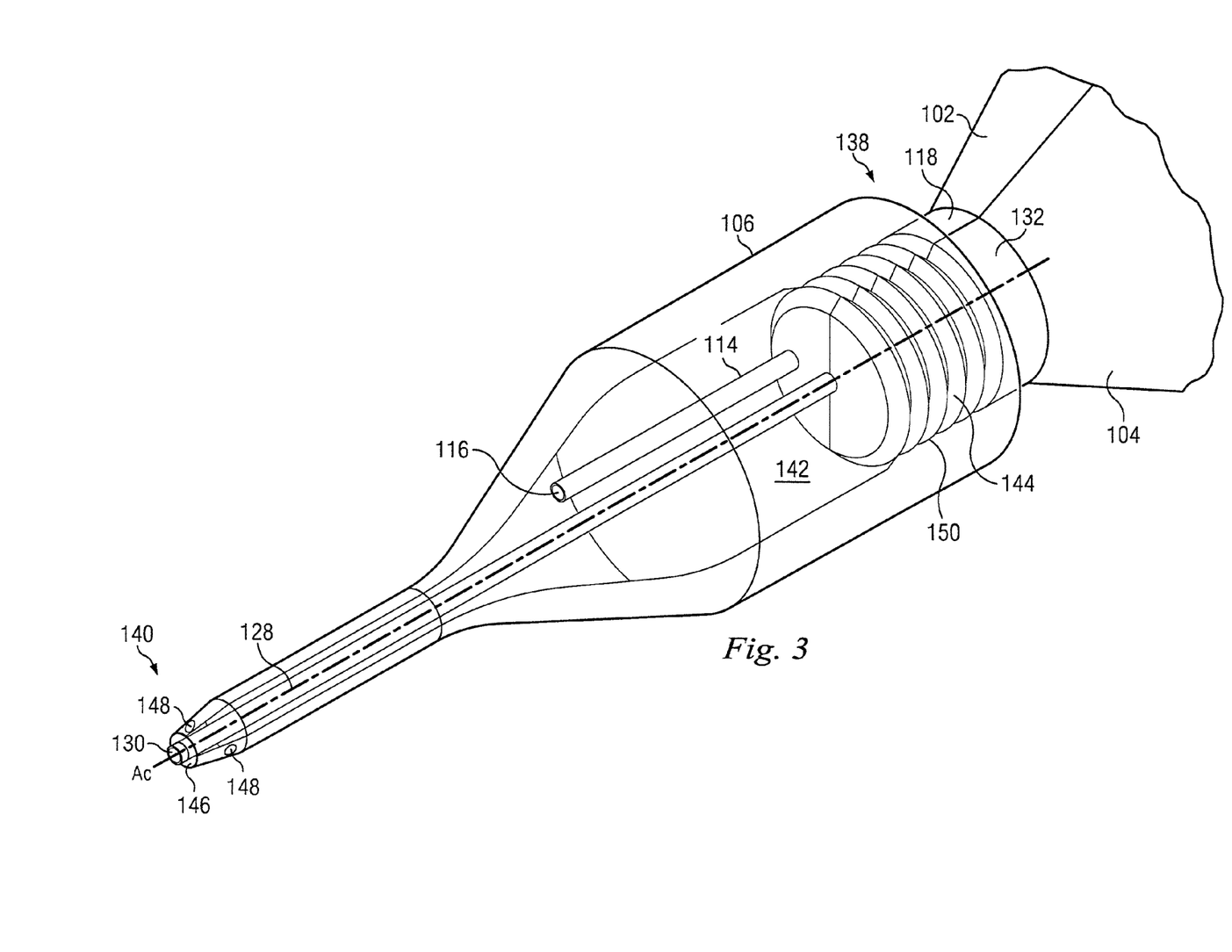
FIG. 3 is an illustration of a perspective view of a distal end of the assembly of FIG. 1.

FIGS. 1-3 show an assembly 100 providing a combined coaxial and bimanual I/A surgical instrument according to one aspect of the present disclosure. The exemplary assembly 100 includes an irrigation hand piece 102, an aspiration hand piece 104, a sleeve member 106, and a coupling member 108.

As shown in FIG. 2, irrigation hand piece 102 gradually tapers from a proximal end 110 to a distal end 112. Extending from distal end 112 is an irrigation needle 114. Irrigation needle 114 is hollow and has a distal opening 116 to provide irrigation fluids therefrom. Although not shown, the irrigation hand piece 102 can be attached to flexible tubing in communication with an irrigation fluid supply. The flexible tubing supplies the irrigation fluid from the irrigation fluid supply to a surgical site through the distal opening 116 of irrigation needle 114.

The irrigation hand piece 102 includes threads 118 on distal end 112 that are positioned adjacent irrigation needle 114. Additionally, irrigation hand piece 102 has a groove 120 near proximal end 112 for receiving coupling member 108. Furthermore, as discussed below, groove 120 may serve as an alignment marker when coupling irrigation hand piece 102 with aspiration hand piece 104. Additionally, irrigation hand piece 102 has a semi-circular cross-section shape. Moreover, irrigation hand piece 102 has a substantially flat planar surface 122 because of the hand piece's semi-circular cross-section shape. Planar surface 122 extends from the proximal end 110 to the distal end 120 of the irrigation hand piece 102. As will be discussed in greater detail below, these features, such as, threads 118, groove 120, and the cross-sectional shape of irrigation hand piece 102, enables assembly 100 to transform or convert between a coaxial I/A device and a bimanual I/A device.

As shown in FIG. 1, the assembly 100 has a first configuration in which the irrigation hand piece 102 and aspiration hand piece 104 are coupled together such that the irrigation needle 114 is substantially parallel to the aspiration needle 128 and the aspiration 128 needle is located along a central axis of the irrigation and aspiration hand pieces 102, 104) as coupled together in the first configuration. As shown in FIG. 2, the assembly 100 has a second configuration in which the irrigation hand piece 102 and aspiration hand piece 104 are uncoupled such that the irrigation needle 114 may not be substantially parallel to the aspiration needle 128 and the aspiration needle 128 is located near a periphery of the aspiration hand piece 104 in the second configuration.

Also shown in FIGS. 1-3, is aspiration hand piece 104. Aspiration hand piece 104 gradually tapers from a proximal end 124 to a distal end 126. Extending from the distal end 126 is an aspiration needle 128. Aspiration needle 128 is hollow and has a distal opening 130. Although not shown, the aspiration hand piece 104 may be attached to a control console by electric cabling and flexible tubing. Through the electric cable, the console varies the power level transmitted by the hand piece to the attached aspiration needle. As such the aspiration needle 128 is vibrated by structure in the hand piece, thereby making the needle a cutting needle. During use within the eye, this vibrating motion causes the aspiration needle 128 to cut eye tissue, such as the lens of a patient's eye. As a result, distal end opening 130 is connected to the flexible tubing to draw lens particulate, other eye tissues, and/or irrigation fluid from the eye through the aspiration needle 128.

The aspiration hand piece 104 includes threads 132 on distal end 126. Threads 132 are positioned adjacent aspiration needle 128. Additionally, aspiration hand piece 104 has a groove 134 near proximal end 124 for receiving coupling member 108. Furthermore, similar to irrigation hand piece 102, aspiration hand piece 104 has a semi-circular cross-section shape.

Moreover, aspiration hand piece 104 has a substantially flat planar surface 136 because of the hand piece's semi-circular cross-section shape. Flat planar surface 136 extends from the proximal end 124 to the distal end 126 of the aspiration hand piece 104. As will be discussed in greater detail below, these features, such as, threads 132, groove 134, and the cross-sectional shape of aspiration hand piece 102, enable assembly 100 to transform or convert between a coaxial and bimanual I/A surgical instrument.

As shown in FIGS. 1-3, irrigation hand piece 102 and aspiration hand piece 104 are removably coupled together by sleeve member 106 and coupling member 108. In such a configuration, irrigation hand piece 102 and aspiration hand piece 104 are aligned such that their respective flat planar surfaces 122 and 136 face each other. In other words, when irrigation hand piece 102 and aspiration hand piece 104 are coupled together their respective flat planer surfaces interface with one another. Moreover, the respective grooves 120 and 134 of irrigation hand piece 102 and aspiration hand piece 104, respectively, act as visual markers to aid in alignment of the two hand pieces when being coupled together.

As best shown in FIG. 3, sleeve member 106 tapers from a proximal end 138 to a distal end 140. Furthermore, sleeve member 106 defines an internal bore 142 therebetween. A proximal opening 144 adjacent the proximal end 138 and a distal opening 146 adjacent the distal end 140 are in communication with internal bore 142. Furthermore, sleeve member 106 includes side openings 148 on distal end 140 that are in communication with internal bore 142.

As shown, proximal opening 144 is sized and shaped to receive the respective distal ends of irrigation and aspiration hand pieces 102 and 104, respectively. In that regard, sleeve member 106 has threads 150 defining the portion of internal bore 142 adjacent proximal opening 144. As such, threads 150 engage with threads 118 and 132 of irrigation and aspiration hand pieces 102 and 104, respectively. Thus, engagement of these threads, in part, couples the irrigation and aspiration hand pieces together.

As shown in FIG. 3, when irrigation and aspiration hand pieces 102 and 104 are coupled, aspiration needle 128 extends along a central axis $A_c$ of sleeve member 106. The central axis $A_c$ extends along the center line of the sleeve member 106. Accordingly, aspiration needle 128 is substantially centrally located within internal bore 142.

Moreover, aspiration needle 128 extends through distal opening 146 of sleeve member 106. For example, aspiration needle 128 may extend about 1 mm beyond the distal opening 146 of sleeve member 106. Furthermore, distal opening 130 of aspiration needle 128 is positioned beyond the distal end 140 of sleeve member 106. As such, aspiration needle 128 is able to aspirate fluids and/or particulate located adjacent distal end 140 of sleeve member 106.

Moreover, as shown in FIG. 3, when irrigation and aspiration hand pieces 102 and 104 are coupled by sleeve member 106, irrigation needle 114 is offset from the central axis $A_c$ of sleeve member 106. In other words, irrigation needle 114 is non-centrally located within internal bore 142. Moreover, irrigation needle 114 remains within internal bore 142 when the sleeve member 106 is coupled to the irrigation and aspiration hand pieces 102 and 104, respectively. As such, distal opening 116 of irrigation needle 114 is positioned within internal bore 142.

During operation, in this configuration, any irrigation fluid emitted from irrigation needle 114 is released within internal bore 142. As discussed above, sleeve member 106 has side openings 148. These side openings on sleeve member 106 direct irrigating fluid out and away from the distal opening 130 of aspiration needle 128. Moreover, distal opening 146 of sleeve member 106 provides an additional pathway for irrigation fluid to be emitted from internal bore 142. Thus, an annular space within bore 142 positioned between aspiration needle 128 and sleeve member 106 along the distal end 140 of sleeve member acts as an irrigation fluid pathway.

As shown in FIG. 1, irrigation and aspiration hand pieces 102 and 104 are further coupled by coupling member 108. Coupling member 108 acts a clip member which is biased towards forcing the irrigation hand piece and aspiration hand piece together. Coupling member 108 is insertable within grooves 120 and 134 of the irrigation and aspiration hand pieces, respectively. Grooves 120 and 134 prevent axial movement of the coupling member 108 along the respective bodies of the irrigation and aspiration hand pieces. Thus, coupling member 108 couples the respective distal ends 110 and 124 of the irrigation and aspiration hand pieces together.

Although coupling member 108 is described as clip member, coupling member 108 is not limited to any particular coupling mechanism. In fact, in other embodiments irrigation hand piece 102 and aspiration hand piece 104 are coupled to each other without the use of coupling member 108. For example, in such alternative embodiments, a coupling mechanism is integrally formed in one or both of irrigation hand piece 102 and aspiration hand piece 104. Such a coupling mechanism may enable the two hand pieces to be coupled by a lock and key, snap fit, press fit, or other coupling arrangement.

In alternative embodiments, surfaces 122 and 136 of irrigation hand piece 102 and aspiration hand piece 104, respectively, are configured with mating profiles of impressions and depressions such that needle 128 is centrally disposed between them when the hand pieces in the coaxial configuration. Furthermore, in other embodiments surfaces 122 and 136 of irrigation hand piece 102 and aspiration hand piece 104, respectively, are substantially non-planar. Such non-planar surfaces are configured to interface with one another by, for example, mating projections and depressions on the non-planar surfaces of the hand pieces. For example, some portions of the surfaces may be planar and other portions of the surfaces non-planar.

As discussed above, irrigation hand piece 102 and aspiration hand piece 104 are coupled together via sleeve member 106 and coupling member 108. FIG. 1 shows this coupled or assembled configuration for assembly 100. In the assembled configuration, assembly 100 is considered a coaxial device 200. In that regard, even though coaxial device 200 can be disassembled as shown in FIG. 2, the coaxial device advantageously acts as a single instrument that perform both irrigation and aspiration functionalities as desired. Moreover, because coaxial device 200 can be held in one hand, a user of the device then has a free hand able to hold an additional instrument.

During operation of coaxial device 200, aspiration needle 128 is able to aspirate fluids and/or particulate located adjacent distal end 140 of sleeve member 106. Moreover, irrigation fluid emitted from irrigation needle 114 is delivered though the annular space between aspiration needle 128 and sleeve member 106 along the distal end 140 of sleeve member 106. The irrigation fluid is emitted from sleeve member 106 though distal opening 146 and side openings 148. Thus, coaxial device 200 is considered coaxial because the aspirated fluids and/or particulates and the irrigation fluids are substantially coaxial while being delivered through the distal end 140 of sleeve member 106.

Unlike traditional coaxial devices, coaxial device 200 can be disassembled to provide a bimanual device. Specifically, FIG. 2 shows that assembly 100, namely irrigation hand piece 102, aspiration hand piece 104, sleeve member 106, and coupling member 108, are physically separable from each other. In that regard, coaxial device 200 (e.g. assembled configuration of assembly 100) can be disassembled by removing sleeve member 106 and coupling member 108 from irrigation hand piece 102 and aspiration hand piece 104. For example, sleeve member 106 can be rotated to disengage the threaded engagement with the distal ends 112 and 126 of irrigation hand piece 102 and aspiration hand piece 104, respectively. Moreover, coupling member 108 can be moved away and/or pulled apart from irrigation hand piece 102 and aspiration hand piece 104. Such movement allows the proximal ends 110 and 124 of the hand pieces to be uncoupled from each other.

Upon disassembly of coaxial device 200, the irrigation hand piece 102, aspiration hand piece 104, sleeve member 106, and coupling member 108 are physically separated from each other. As such a surgeon is able to independently use the irrigation hand piece 102 and aspiration hand piece 104. Moreover, because the irrigation hand piece 102 and aspiration hand piece 104 are separate, the flow of the fluids and/or particulates aspirated and the irrigated fluid are non-coaxial. Accordingly, assembly 100 in the disassembled configuration provides physically separable and independently operable irrigation hand piece 102 and aspiration hand piece 104 that act as a bimanual instrument.

As discussed above, because irrigation hand piece 102 and aspiration hand piece 104 acts as a bimanual instrument when assembly 100 is disassembled, a surgeon can make two smaller separate incisions into the eye. As such the surgeon can insert the aspiration needle 128 into one of the incision sites and the irrigation needle 116 into the other of the incision sites. This allows for smaller incision sizes in the eye when compared to the phacoemulsification procedure using the coaxial device 200 discussed above. Moreover, because the aspiration hand piece 104 is not coupled to the irrigation hand piece 102, the diameter of the distal end 126 of the aspiration instrument is smaller than the distal end of the coaxial device 200 (e.g. diameter of sleeve member 106). Again, this allows for a smaller incision size for insertion of the aspiration needle 128 into the eye when compared to the phacoemulsification procedure using the coaxial device 200.

Based on the foregoing, assembly 100 provides many unique advantages. Assembly 100 provides a surgeon the capability of both a coaxial device and a bimanual device. The surgeon advantageously has the choice and can freely configure assembly 100 between its assembled configuration (e.g. coaxial device) and its disassembled configuration (e.g. bimanual device) as needed. For example, the surgeon can configure assembly 100 into coaxial device 200 in order to have a free or unoccupied hand while performing a procedure. Additionally, the surgeon can configure assembly 100 into the disassembled bimanual configuration in order to be able to insert the irrigation and/or aspiration hand piece through a smaller incision size. Furthermore, because assembly 100 provides both the capable of both a coaxial and bimanual devices, the surgeon no longer has to stock both types of devices. In addition, assembly 100 provides further cost saving measures because the surgeon no longer has to open and use two separate coaxial and bimanual devices to achieve a desired result. Thus, assembly 100 provides many advantageous to a surgeon over a traditional coaxial device and/or bimanual device.

Figure 4:
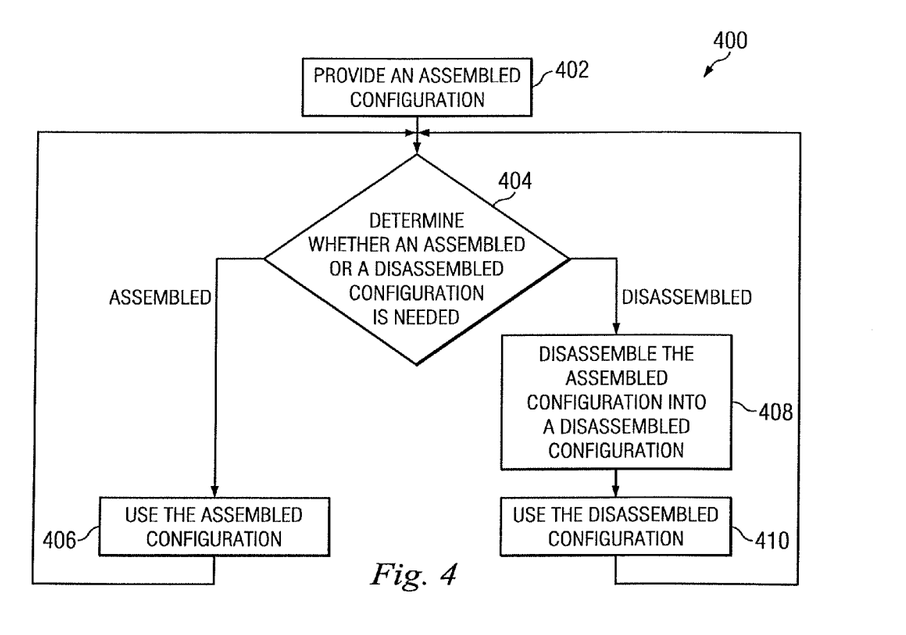
FIG. 4 is a flow diagram showing exemplary steps for using the assembly of FIG. 1 beginning with an assembled configuration.

FIG. 4 is a flow diagram showing a method for using assembly 100 beginning with an assembled configuration of assembly 100. For example, method 400 may be used before, during, or after an ophthalmic surgery, such as a phacoemulsification procedure. Method 400 begins with step 402 by providing assembly 100 in an assembled configuration. As discussed above, the assembled configuration is considered coaxial device 200.

At step 404, a determination is made whether a coaxial device or a bimanual device is needed for a particular surgical step and/or procedure. As discussed above, may factors may influence this determination. For example, a user may determine that they need a free hand. Thus, the use of coaxial device 200 would allow the user to have a free hand. Additionally, a user may prefer a smaller incision size. The disassembled bimanual configuration of assembly 100 would allow a user to have a smaller incision size.

When the user determines that a coaxial device 200 is needed, the method continues to step 406. At step 406, the coaxial device 200 is used by the user. After the coaxial device has been used at step 406, the method returns to step 404. Accordingly, even though the user selected a coaxial device 200 for use during a particular surgical step or method, the user can change configurations of assembly 100 before, during, or after any particular surgical step and/or procedure.

Returning to step 404, when the user determines that the disassembled bimanual configuration of assembly 100 is needed, the method continues to step 408. At step 408, unlike traditional coaxial devices, coaxial device 200 can be disassembled to provide a bimanual device. Specifically, the coaxial device 200 (e.g. assembled configuration of assembly 100) can be disassembled by removing sleeve member 106 and coupling member 108 from irrigation hand piece 102 and aspiration hand piece 104. For example, sleeve member 106 can be rotated to disengage the threaded engagement with distal ends 112 and 126 of irrigation hand piece 102 and aspiration hand piece 104, respectively. Moreover, coupling member 108 can be removed by pulling or moving the coupling member away from both the irrigation hand piece 102 and aspiration hand piece 104. After removal of sleeve member 106 and coupling member 108, the hand pieces are uncoupled from each other.

Accordingly, at step 410, upon disassembly of coaxial device 200, the irrigation hand piece 102, aspiration hand piece 104, sleeve member 106, and coupling member 108 are physically separated from each other. As such a surgeon is able to independently use the irrigation hand piece 102 and aspiration hand piece 104. Accordingly, assembly 100 in the disassembled configuration provides physically separable and independently operable irrigation hand piece 102 and aspiration hand piece 104 that act as a bimanual device.

After the disassembled bimanual configuration of assembly 100 has been used at step 410, the method returns to step 404. Accordingly, even though the user selected the disassembled bimanual configuration of assembly 100 for use during a particular surgical step or method, the user can change configurations of assembly 100 before, during, or after any particular surgical step and/or procedure.

Figure 5:
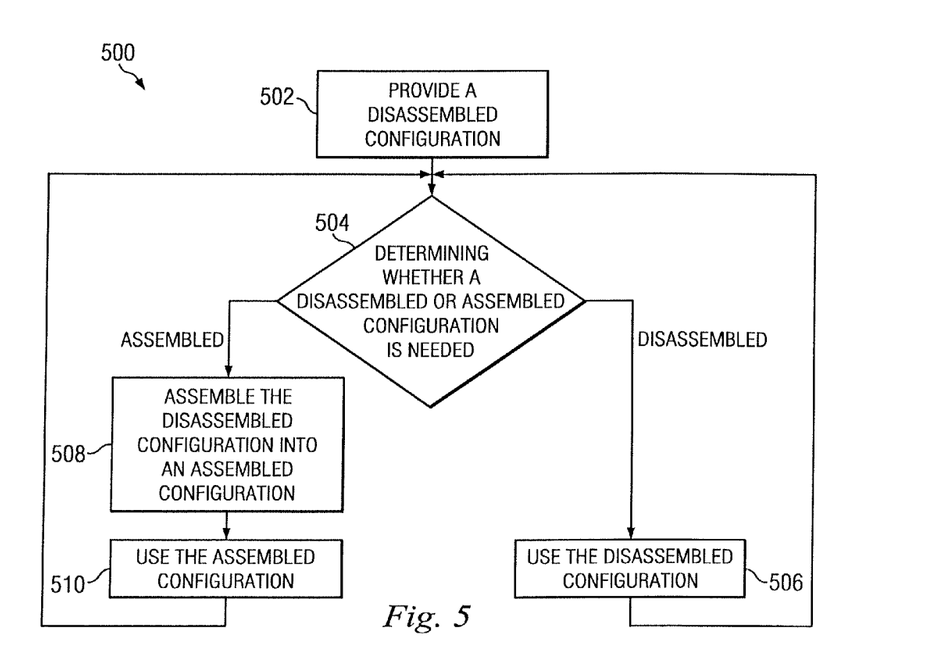
FIG. 5 is a flow diagram showing exemplary steps for using the assembly of FIG. 1 beginning with a disassembled configuration.

FIG. 5 is a flow diagram showing an exemplary method 500 for using assembly 100 beginning with a disassembled configuration of assembly 100. For example, method 500 may be used before, during, or after an ophthalmic surgery, such as a phacoemulsification surgery. Method 500 begins with step 502 by providing assembly 100 in a disassembled configuration.

At step 504, a determination is made whether the disassembled bimanual configuration or an assembled coaxial configuration is needed for a particular surgical step and/or procedure. As discussed above, may factors may influence this determination. For example, a user may determine that they need a free hand. Thus, the use of coaxial device 200 would allow the user to have a free hand. Additionally, a user may prefer a smaller incision size. The disassembled bimanual configuration of assembly 100 would allow a user to have a smaller incision size.

When the user determines that the disassembled bimanual configuration is needed, the method continues to step 506. At step 506, the disassembled bimanual configuration is used by the user. After the disassembled bimanual configuration has been used at step 506, the method returns to step 504. Accordingly, even though the user selected the disassembled bimanual configuration for use during a particular surgical step or method, the user can change configurations of assembly 100 before, during, or after any particular surgical step and/or procedure.

Returning to step 504, when the user determines that the assembled coaxial configuration of assembly 100 is needed, the method continues to step 508. At step 508, unlike traditional bimanual devices, assembly 100 can be assembled to provide a coaxial device. In other words, the disassembled bimanual configuration can be assembled into the coaxial device 200. Such assembly can include coupling irrigation hand piece 102 and aspiration hand piece 104 together by sleeve member 106 and coupling member 108.

In such a configuration, irrigation hand piece 102 and aspiration hand piece 104 are aligned relative to each other. For example, the respective planar surface 122 and 136 of the hand pieces face each other when the irrigation hand piece 102 and aspiration hand piece 104 are aligned. Moreover, to aid in the alignment of irrigation hand piece 102 and aspiration hand piece 104, the respective grooves 120 and 134 can act as visual markers.

Upon alignment of irrigation hand piece 102 and aspiration hand piece 104, sleeve member 106 can be use to threadedly engage the distal, ends 112 and 126 of irrigation hand piece 102 and aspiration hand piece 104, respectively. Moreover, coupling member 108 can be inserted into grooves 120 and 134 of the respective hand pieces to further couple the proximal ends of the hand pieces. Thus, when coupled together, the irrigation hand piece 102 and aspiration hand piece 104 combine to provide coaxial device 200 a substantially circular cross-section shape.

Accordingly, at step 510, upon assembly of the coaxial device 200, the irrigation hand piece 102, aspiration hand piece 104, sleeve member 106, and coupling member 108 are connected to each other and act as a single coaxial device. As such, a surgeon is able to hold and use coaxial device 200 for irrigation and aspiration purposes with one hand while keeping the other hand available for use with another surgical instrument or for any other purpose.

After the assembled coaxial device 200 has been used at step 510, the method returns to step 504. Accordingly, even though the user selected the assembled coaxial device configuration of assembly 100 for use during a particular surgical step or method, the user can change configurations of assembly 100 before, during, or after any particular surgical step and/or procedure.

In summary, as discussed above, assembly 100 provides many unique advantages. Assembly 100 provides a surgeon the capability of both a coaxial device and a bimanual device. The surgeon advantageously has the choice and can freely configure assembly 100 between its assembled configuration (e.g. coaxial device) and its disassembled configuration (e.g. bimanual device) as needed. For example, the surgeon can configure assembly 100 into coaxial device 200 in order to have a free or unoccupied hand while performing a procedure. Additionally, the surgeon can configure assembly 100 into the disassembled bimanual configuration in order to be able to insert the irrigation and/or aspiration hand piece through a smaller incision size as compared to the incision size necessary for a coaxial device. Furthermore, because assembly 100 provides both the capability of both a coaxial and bimanual device, the surgeon no longer has to carry inventory for both types of devices. In addition, assembly 100 provides further cost saving measures because the surgeon no longer has to open and use two separate coaxial and bimanual devices. Thus, assembly 100 provides many advantageous to a surgeon over a traditional coaxial device and/or bimanual device.

While the present disclosure has been illustrated by the above description of embodiments, and while the embodiments have been described in some detail, it is not the intention of the applicants to restrict or in any way limit the scope of the present disclosure to such detail. Additional advantages and modifications will readily appear to those skilled in the art. Therefore, the present disclosure in its broader aspects is not limited to the specific details, representative apparatus and methods, and illustrative examples shown and described. Accordingly, departures may be made from such details without departing from the spirit or scope of the applicant's general or inventive concept.

I claim:

1. An assembly comprising:
    an irrigation hand piece including an irrigation needle extending from a distal end of the irrigation hand piece, the irrigation needle configured to release an irrigation fluid from the assembly;
    an aspiration hand piece including an aspiration needle extending from a distal end of the aspiration hand piece, the aspiration needle having an axis and being configured to aspirate an aspirated fluid into the assembly; and
    a sleeve member, the sleeve member coupling the irrigation hand piece and the aspiration hand piece together when the assembly is in the first configuration wherein the sleeve member has an internal bore and the distal ends of the aspiration and irrigation hand pieces are configured to extend into the bore to couple the distal ends of the aspiration and irrigation hand pieces to the sleeve member;
    wherein the assembly has a first configuration in which the irrigation hand piece and aspiration hand piece are coupled together such that the irrigation needle is substantially parallel to the aspiration needle and the aspiration needle is located along a central axis of the irrigation and aspiration hand pieces in the first configuration and a second configuration in which the irrigation hand piece and aspiration hand piece are uncoupled such that the irrigation needle is not substantially parallel to the aspiration needle and the aspiration needle is located near a periphery of the aspiration hand piece in the second configuration.

2. The assembly of claim 1, wherein the internal bore has a proximal opening and opposing distal opening, the sleeve member having internal threads within the bore adjacent the proximal opening, and
    wherein the distal ends of the aspiration and irrigation hand pieces each have external threads that threadedly engage the internal threads within the bore.

3. The assembly of claim 2, wherein a portion of the aspiration needle extends beyond the distal opening.

4. The assembly of claim 1, wherein a distal tip of the irrigation needle is positioned within the internal bore.

5. The assembly of claim 1, wherein the aspiration needle extends substantially along a central axis of the sleeve member.

6. The assembly of claim 1, wherein the irrigation needle is offset from the central axis of the sleeve member.

7. The assembly of claim 1, further comprising a coupling member extending between the irrigation hand piece and the aspiration hand piece to couple the hand pieces together when the assembly is in the first configuration.

8. The assembly of claim 7, wherein the coupling member is a clip member that couples a proximal end portion of each of the irrigation hand piece and the aspiration hand piece together.

9. An assembly comprising:
- an irrigation hand piece including an irrigation needle extending from a distal end of the irrigation hand piece, the irrigation needle configured to release an irrigation fluid from the assembly;
- an aspiration hand piece including an aspiration needle extending from a distal end of the aspiration hand piece, the aspiration needle having an axis and being configured to aspirate an aspirated fluid into the assembly; and
- a sleeve member selectively attachable to the irrigation and aspiration hand pieces and shaped so that when in a first configuration the sleeve member couples the irrigation hand piece and the aspiration hand piece together such that the irrigation needle is substantially parallel to the aspiration needle and the aspiration needle is located along a central axis of the irrigation and aspiration hand pieces in the first configuration and a second configuration detached from the irrigation hand piece and the aspiration hand piece such that the irrigation needle is not substantially parallel to the aspiration needle and the aspiration needle is located near a periphery of the aspiration hand piece in the second configuration; wherein the sleeve member has an internal bore such that in the first configuration a distal end of each of the aspiration and irrigation hand pieces extends into the internal bore to couple the sleeve member.

10. The assembly of claim 9, wherein the aspiration needle extends through the internal bore substantially along a central axis of the sleeve member such that a distal tip of the needle extends beyond the bore, and
wherein the irrigation needle is offset from the central axis of the sleeve member and a distal tip of the irrigation needle is positioned within the internal bore.

11. The assembly of claim 9, wherein the irrigation hand piece and aspiration hand piece each have a substantially semi-circular cross-section shape such that when the sleeve is in the first configuration the assembly has a substantially circular cross-section shape.

12. An assembly comprising:
- an irrigation hand piece including an irrigation needle extending from a distal end of the irrigation hand piece, the irrigation needle configured to release an irrigation fluid from the assembly;
- an aspiration hand piece including an aspiration needle extending from a distal end of the aspiration hand piece, the aspiration needle having an axis and being configured to aspirate an aspirated fluid into the assembly; and
- a sleeve member selectively attachable to the irrigation and aspiration hand pieces and shaped so that when in a first configuration the sleeve member couples the irrigation hand piece and the aspiration hand piece together such that the irrigation needle is substantially parallel to the aspiration needle and the aspiration needle is located along a central axis of the irrigation and aspiration hand pieces in the first configuration and a second configuration detached from the irrigation hand piece and the aspiration hand piece such that the irrigation needle is not substantially parallel to the aspiration needle and the aspiration needle is located near a periphery of the aspiration hand piece in the second configuration; wherein the irrigation hand piece and aspiration hand piece each have a substantially semi-circular cross-section shape such that when the sleeve is in the first configuration the assembly has a substantially circular cross-section shape; and wherein the sleeve member has an internal bore such that in the first configuration a distal end of each of the aspiration and irrigation hand pieces extends into the internal bore to couple the sleeve member.

13. The assembly of claim 12, wherein the aspiration needle extends through the internal bore substantially along a central axis of the sleeve member such that a distal tip of the needle extends beyond the bore, and
wherein the irrigation needle is offset from the central axis of the sleeve member and a distal tip of the irrigation needle is positioned within the internal bore.

* * * * *